US009994900B2

(12) United States Patent
Mansour et al.

(10) Patent No.: US 9,994,900 B2
(45) Date of Patent: Jun. 12, 2018

(54) COMPOSITE BIOMARKERS FOR NON-INVASIVE SCREENING, DIAGNOSIS AND PROGNOSIS OF COLORECTAL CANCER

(71) Applicant: King Abdullah University of Science and Technology, Thuwal (SA)

(72) Inventors: Hicham Mansour, Thuwal (SA); Roberto Incitti, Thuwal (SA); Vladimir Bajic, Thuwal (SA)

(73) Assignee: King Abdullah University of Science and Technology, Thuwal (SA)

(*) Notice: Subject to any disclaimer, the term of this patent is extended or adjusted under 35 U.S.C. 154(b) by 655 days.

(21) Appl. No.: 14/352,661

(22) PCT Filed: Oct. 16, 2012

(86) PCT No.: PCT/IB2012/002515

§ 371 (c)(1),
(2) Date: Apr. 17, 2014

(87) PCT Pub. No.: WO2013/057581

PCT Pub. Date: Apr. 25, 2013

(65) Prior Publication Data

US 2014/0255418 A1 Sep. 11, 2014

Related U.S. Application Data

(60) Provisional application No. 61/548,202, filed on Oct. 17, 2011.

(51) Int. Cl.
*C12Q 1/68* (2018.01)

(52) U.S. Cl.
CPC ......... *C12Q 1/6883* (2013.01); *C12Q 1/6886* (2013.01); *C12Q 2600/154* (2013.01)

(58) Field of Classification Search
None
See application file for complete search history.

(56) References Cited

FOREIGN PATENT DOCUMENTS

| | | | |
|---|---|---|---|
| WO | 2003072821 | A2 | 9/2003 |
| WO | 2005001140 | A2 | 1/2005 |
| WO | WO 2007/140319 | | 12/2007 |
| WO | WO 2008/102002 | | 8/2008 |

OTHER PUBLICATIONS van Eijk et al. BMC Genomics 2012, 13:636, thirteen pages.*
Costello et al (1994) The Journal of Biological Chemistry, vol. 269, No. 25, pp. 17228-17237, 1994.*
Wu (2001) Journal of Pathology, 195:53-65.*
Newton et al (2001) Journal of Computational Biology, vol. 8, No. 1, 2001, p. 37-52.*
Slonin, Nature Genetics Supplement, vol. 32, Dec. 2002, pp. 502-508.*
Baker. Journal of the National Cancer Institute, vol. 95, No. 7, Apr. 2, 2003.*
Whitehead (Genome Biology 2005 vol. 6 Issue 2 Article R13).*
Bock (Epigenomics 2009 vol. 1 No. 1 pp. 99-110).*
Michels (Experimental Gerontology 2010 vol. 45 pp. 297-301).*
Hesselink et al. Clin Cancer Res, 2011; 17:2459-2465.*
Bock et al. (Nature Biotechnology, vol. 28, No. 10, pp. 1106-1114, plus Online Methods, 2 pages), 2010.*
Oster et al. (International Journal of Cancer; 129, 2855-2866 (2011) published on line Mar. 11, 2011).*
Bjorklund et al. (Abstract OR20-1, The Endocrine Society's 92nd Annual Meeting, Jun. 19-22, 2010, three pages).*
Bazensky et al. (MEDSURG Nursing, Feb. 2007, vol. 16, No. 1, pp. 46-51).*
Kibriya et al., "A genome-wide DNA methylation study in colorectal carcinoma", BMC Medical Genomics. Biomed Central Ltd. vol. 4. No. 1. Jun. 23, 2011 (Jun. 23, 2011), p. 50, London UK.
Xu et al., "Methylation profile of the promoter CpG islands of 31 genes that may contribute to colorectal carcinogenesis", World J Gastroenterol, vol. 10, No. 23, Jan. 1, 2004 (Jan. 1, 2004), pp. 3441-3454.
Cheng et al., "Multiplexed profiling of candidate genes for CpG island methylation status using a flexible PCR/LDR/Universal Array assay", Genome Research, vol. 16, No. 2, Feb. 1, 2006 (Feb. 1, 2006), pp. 282-289, Cold Spring Harbor Laboratory Press. Woodbury. NY. US.
Ishiguro et al., "Influence of methylated p15 INK4b and p16 INK4a genes on clinicopathological features in colorectal cancer", Journal of Gastroenterology and Hepatology, vol. 21, No. 8, Aug. 1, 2006 (Aug. 1, 2006), pp. 1334-1339.
Illumina: "Whole-genome expression analysis using the Sentrix Human-6 and HumanRef-8 expression beadchips", Jun. 28, 2005 (Jun. 28, 2005), pp. 1-8, URL: http://res.illumina.com/documents/products/techbulletins/techbulletin_whole_genome_expression.pdf.
Affymetrix: "GeneChip TM Human Genome U133 Arrays", Datasheet Affymetrix, Jan. 1, 2003 (Jan. 1, 2003), pp. 1-8.
Agilent Technologies: "Agilent SurePrint G3 Human Catalog CGH Microarrays", Jan. 8, 2009 (Jan. 8, 2009), pp. 1-8, URL:http://www.chem.agilent.com/Library/brochures/5990-3368en_lo.pdf.
Illumina: "Infinium HumanMethylation27, RevB BeadChip Kits", Feb. 8, 2011 (Feb. 8, 2011), pp. 1-2, URL: http://www.illumina.com/products/methylation_450_beadchip_kits.ilmn.
Kim et al., "Epigenomic Analysis of Aberrantly Methylated Genes in Colorectal Cancer Identifies Genes Commonly Affected by Epigenetic Alterations", *Annals of Surgical Oncology*, 18(8): 2338-2347, 2011.

(Continued)

*Primary Examiner* — Juliet C Switzer
(74) *Attorney, Agent, or Firm* — Smith, Gambrell & Russell, LLP

(57) ABSTRACT

The present invention concerns particular biomarkers for diagnosing and/or prognosticating colorectal cancer, in particular in a non-invasive manner. The methods and compositions concern analysis of methylation patterns of one or more genes from a set of 29 genes identified as described herein. In certain embodiments, the gene set includes at least P15.INK4b, SST, GAS7, CNRIP1, and PIK3CG.

12 Claims, 1 Drawing Sheet

(56) References Cited

OTHER PUBLICATIONS

Mori et al., "A Genome-Wide Search Identifies Epigenetic Silencing of Somatostatin, Tachykinin-1, and 5 Other Genes in Colon Cancer", *Gastroenterology*, Elsevier, Philadelphia, PA, 131(3): 797-808, 2006.

Oster et al., "Identification and validation of highly frequent CpG island hypermethylation in colorectal adenomas and carcinomas", *International Journal of Cancer*, 129(12): 2855-2866, 2011.

Lind et al., "Identification of an epigenetic biomarker panel with high sensitivity and specificity for colorectal cancer and adenomas", *Molecular Cancer*, 10(1): 85, 2011.

Semba et al., "Down-Regulation of PIK3CG, a Catalytic Subunit of Phosphatidylinositol 3-OH Kinase, by CpG Hypermethylation in Human Colorectal Carcinoma", *Clinical Cancer Research*, 8: 3824-3831, 2002.

* cited by examiner

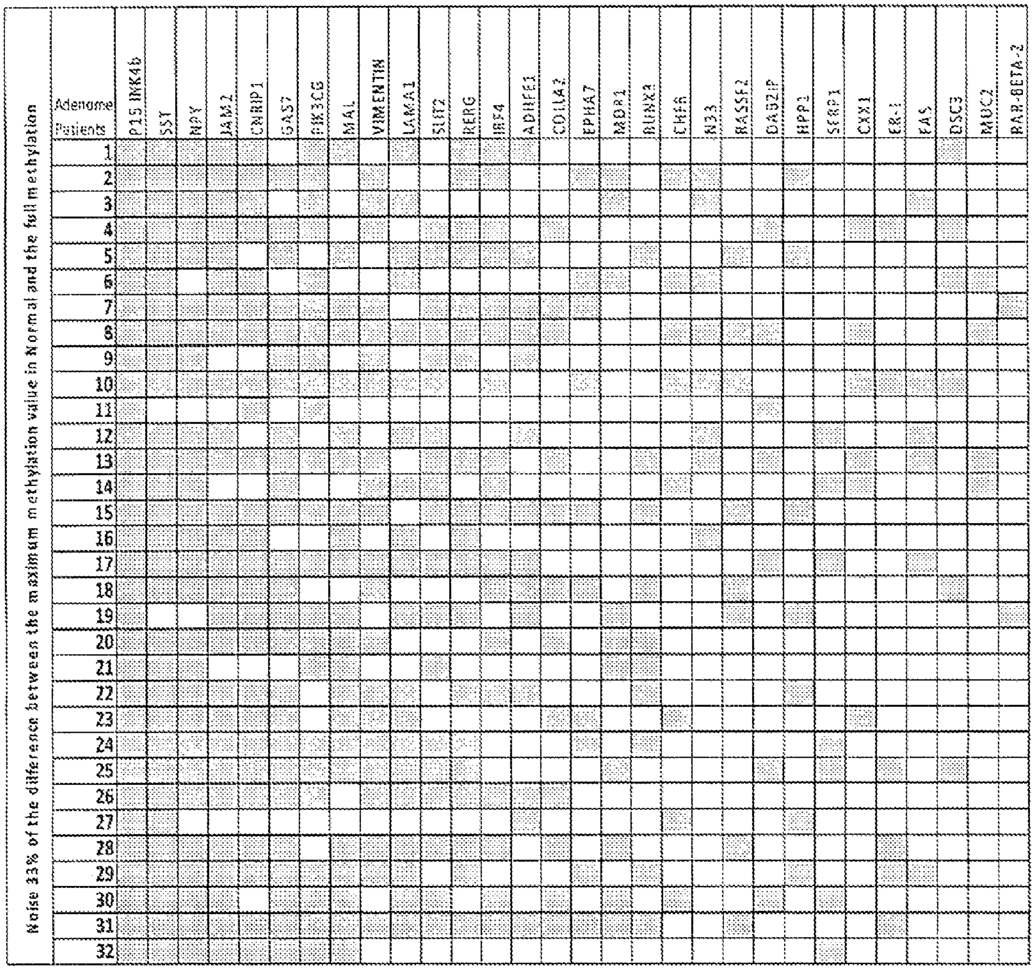
Noise 33% of the difference between the maximum methylation value in Normal and the full methylation
Adenome Patients
P15 INK4b
SST
NPY
JAM2
CNRIP1
GAS7
PIK3CG
MAL
VIMENTIN
LAMA1
SLIT2
RERG
IRF4
ADHFE1
COL1A2
EPHA7
MDR1
RUNX3
CHFR
N33
RASSF2
DAB2IP
HPP1
SFRP1
CXX1
ER-1
FAS
DSC3
MBC2
RAR-BETA-2
1
2
3
4
5
6
7
8
9
10
11
12
13
14
15
16
17
18
19
20
21
22
23
24
25
26
27
28
29
30
31
32

COMPOSITE BIOMARKERS FOR NON-INVASIVE SCREENING, DIAGNOSIS AND PROGNOSIS OF COLORECTAL CANCER

CROSS REFERENCE TO RELATED APPLICATIONS

This application is a national phase application under 35 U.S.C. § 371 that claims priority to PCT Application No. PCT/IB2012/002515 filed on Oct. 16, 2012, which claims priority to U.S. Provisional Patent Application Ser. No. 61/548,202, filed Oct. 17, 2011, which are incorporated by reference herein in their entirety.

TECHNICAL FIELD

The present invention concerns at least the fields of molecular biology, cell biology, and medicine, including cancer medicine.

BACKGROUND OF THE INVENTION

Despite the increasing body of knowledge and the growing development of specific therapies and diagnostic tools, colorectal cancer (CRC) remains the second leading cause of malignant mortality in industrialized nations, accounting for more than 13% of all cancer deaths (Remontet et al. Evolution de l'incidence de la mortalite par cancer 2003; www.insv.sante.fr, Cancer Incidence and Mortality Worldwide, Globocan 2008, WHO). The relative survival rates (ratio of observed survival over the expected survival in a group of people with the same gender and age) depend on the stage of CRC at diagnosis. Stage I tumours are associated with the highest relative survival rate, while those of stage 1V, known as poor prognosis (SEER 2006, O'Connell et al. 2004) with the lowest survival rate. Unfortunately, most cases of CRC are diagnosed in the already advanced stages when a curative surgical treatment is not possible, and chemotherapy remains the only option in spite of high costs and undesirable side effects. Because of the absence of efficient diagnostic methods of CRC, patients with colorectal neoplasia would most benefit from efficient early diagnostic CRC tests that can reveal early stages of CRC, thereby enabling preventive interventions.

The risk of CRC begins to increase after the age of 50; thereafter the risk continues to rise, approximately doubling with each succeeding decade (NCI-2006). Increased risk is slower in women and, before age 75, women have a lower incidence of CRC than men (Boyle P et al 2007). The desirable tests comprise as many as possible of the following features: average-risk, asymptomatic individuals, highly sensitive, non-invasive, low-risk, cost-effective, and ease of implementation across a large population. In many European countries, such as France, the Hemoccult gaiac test is currently recommended in screening campaigns as the first step: tests on three consecutive stool samples to detect occult blood. If the results are positive, this is followed by a second step: a colonoscopy to detect colorectal tumours. In the field of screening, blood tests are generally better accepted than faecal tests. However, no formal seric test is currently available for CRC. The development of the first assays of serum carcinoembryonic antigen (CEA) in 1965 raised considerable hope on the possibility of screening test in blood (Gold et al 1965, Thompson et al 1969). However, subsequent work showed that the sensitivity of CEA was less than 35% in individuals with invasive cancer; it could not detect early forms and its specificity was insufficient, since its serum levels increase in several pathologies. The limitations of the CA19-9 antigen, introduced more recently (Ritts 1984), are comparable to those of CEA. The current use of these two molecules is limited to post-therapeutic surveillance.

DNA methylation plays a substantial role in colorectal cancer (CRC) development. It induces a change of transcriptome profile in epithelial colon cells. The down-regulation of some genes is induced by the methylation mechanism of CpG islands in their promoters, which inhibits the ability of transcription factors to induce the expression of the target genes. In addition to the role of the involvement of methylation mechanism in the genomic instability of colon epithelial cells during the CRC development, the methylation pattern of some genes is useful to screen and detect patients having different stages of CRC. A convenience is that such methylation tests can be done using body fluids, such as serum and others. The present invention satisfies a need in the art to provide biomarkers for colorectal cancer screening that are highly sensitive and specific.

BRIEF SUMMARY OF THE INVENTION

The present invention is directed to methods and compositions that provide screening, diagnosis, and/or prognosis of cancer, including colorectal cancer. In some embodiments, the methods are non-invasive for colorectal cancer. The cancer may occur in a human mammal, although other mammals are encompassed in the invention, including dogs, cats, horses, and so forth.

Embodiments of the present invention provide methods and compositions for colorectal cancer (CRC) screening, diagnosis and/or prognosis, and in specific embodiments the invention relates to particular expression patterns for CRC screening, diagnosis and/or prognosis. In specific embodiments, the combination of particular methylation patterns of a variety of biomarkers for CRC screening, diagnosis and/or prognosis is provided. These markers can be tested in body fluids (such as serum, plasma, urine, spittle, sputum and/or stool, for example) of patients with CRC. The biomarker set of genes to be assayed comprises, consists essentially of, or consists of one or more of P15.INK4b (also referred to as CDKN2B cyclin-dependent kinase inhibitor 2BP15; MTS2; TP15; CDK4I; INK4B; p15INK4b), SST (also referred to as SMST), NPY (also referred to as neuropeptide Y; PYY4), JAM2 (also referred to as junctional adhesion molecule 2; JAMB; CD322; JAM-B; VEJAM; PRO245; VE-JAM; C21orf43), CNRIP1 (also referred to as cannabinoid receptor interacting protein 1; CRIP1; C2orf32; DKFZp566K1924), GAS7 (also referred to as growth arrest-specific 7; MGC1348; KIAA0394; MLL/GAS7), PIK3CG (also referred to as phosphoinositide-3-kinase, catalytic, gamma polypeptide; PI3K; PIK3; PI3CG; PI3 Kgamma), MAL (also referred to as mal, T-cell differentiation protein), LAMA1 (also referred to as laminin, alpha 1; LAMA; S-LAM-alpha), SLIT2 (also referred to as slit homolog 2; SLIL3; Slit-2; FLJ14420), RERG (also referred to as RAS-like, estrogen-regulated, growth inhibitor; MGC15754), IRF4 (also referred to as interferon regulatory factor 4; MUM1; LSIRF), ADHFE1 (also referred to as alcohol dehydrogenase, iron containing, 1; HOT; ADH8; FLJ32430; HMFT2263; MGC48605), COL1A2 (also referred to as collagen, type I, alpha 2; OI4), EPHA7 (also referred to as EPH receptor A7; EHK3; HEK11), RUNX3 (also referred to as runt-related transcription factor 3; AML2; CBFA3; PEBP2aC; FLJ34510; MGC16070), MDR1 (also referred to as ATP-binding cassette, sub-family B (MDR/TAP), member 1; CLCS; MDR1; P-GP; PGY1; ABC20; CD243; GP170; MGC163296), CHFR (also referred to as checkpoint with forkhead and ring finger domains; RNF116; RNF196; FLJ10796; FLJ33629), TUSC3 (also referred to as N33 and tumor suppressor candidate 3; M33; N33; MRT7; OST3A; D8S1992; MGC13453; DKFZp686B22120), RASSF2 (also known as Ras association (RalGDSAF-6) domain family member 2; CENP-34; KIAA0168; RASFADIN; DKFZp781O1747), DAB21P (also known as DAB2 interacting protein; AIP1; AF9Q34; DIP1/2; FLJ39072; KIAA1743), HPP1 (also known as transmembrane protein with EGF-like and two follistatin-like domains 2; TR; HPP1; TPEF; TENB2; CT120.2), SFRP1 (also referred to as secreted frizzled-related protein 1; FRP; FRP1; FrzA; FRP-1; SARP2), CXX1 (also referred to as family with sequence similarity 127, member A; family with sequence similarity 127, member A; Mar8; MAR8c; Mart8; MART8C; MGC117411), Estrogen receptor 1 (also known as ER; ESR; ESR1; Era; ESRA; NR3A1; DKFZp686N23123), FAS (also referred to as Fas (TNF receptor superfamily, member 6); APT1; CD95; FAS1; APO-1; FASTM; ALPS1A; TNFRSF6), DSC3 (also referred to as desmocollin 3; DSC; DSC1; DSC2; DSC4; CDHF3; HT-CP), MUC2 (also referred to as mucin 2, oligomeric mucusgel-forming; MLP; SMUC; MUC-2), and retinoic receptor acid beta 2 (also known as RARB HAP; RRB2; NR1B2) genes. In specific embodiments, the biomarker set comprises one or more of the following genes: JAM2, LAMA1 P15-INK4b, SST, NPY, MAL, MDR1, RUNX3, ADHFE1, CNRIP1, GAS7, IRF4, SLIT2 and RERG. In specific embodiments, the biomarker set comprises one or more of the following genes: JAM2, LAMA1 P15-INK4b, SST, NPY, MAL, CNRIP1, GAS7, SLIT2, PIK3CG, and RERG. In certain aspects, the methylation of one or more of the regulatory regions of one or more of the aforementioned genes is assayed in methods of the invention.

Thus, in specific embodiments, the methylation patterns of different subsets of particular genes enable sufficiently accurate screening, diagnosis and/or prognosis of CRC. In some embodiments, one can use combinations of the methylation patterns of genes that belong to the same signaling pathways as any of the listed genes provided herein and the methylation pattern thereof to significantly improve accuracy of screening, diagnosis and/or prognosis of CRC.

In some embodiments, the combination of the methylation patterns of at least two particular genes provides a screening, diagnostic and prognostic marker set for CRC, although in some cases the combination of 3, 4, 5, 6, 7, 8, 9, 10, 11, 12, 13, 14, 15, 16, 17, 18, 19, 20, 21, 22, 23, 24, 25, 26, 27, 28, or 29 genes is employed.

Methods may employ assaying of tissue, blood, serum, plasma, spittle, stool, urine, or any other body fluid, for example. Any appropriate method may be used to assess the target directly in the biospecimen (because the extraction step could be skipped in some cases) or extract and concentrate nucleic acids from body fluids, such as silica column, silica beads, phenol chloroform method, or any beads or columns enabled to concentrate nucleic acids). Any appropriate method may be used to target the specific nucleic acids that correspond to the particular genes using normal or labeled oligonucleotides, such as Sybergreen, HRM dyes, Taqman or Fret (Fluorescence Resonance Energy Transfer) chemistries, for example. Any appropriate method may be used to ascertain the level of methylation of the target sequences, such as methylight PCR (such as AB, Roche, Qiagen; Valencia, Calif.), methylation array (Illumina, Agilent, Affymetrix), methylation sequencing (Illumina, AB, Roche, Helicos, Pacific Bio), methyl-beaming (using flow cytometry), mass spectrometry, a combination thereof, and so forth.

The present invention includes diagnosing colorectal cancer by assaying methylation status of JAM2, LAMA1 P15-INK4b, SST, NPY, MAL, MDR1, RUNX3, ADHFE1, CNRIP1, GAS7, IRF4, SLIT2 and RERG genes.

In some embodiments, there is a method for screening, diagnosing, and/or prognosticating colorectal cancer in an individual, comprising the steps of obtaining a sample from the individual; and assaying the sample for methylation status of at least two, at least three, at least four, or all of the following genes: P15.INK4b, somatostatin, GAS7, CNRIP1, and PIK3CG. Methods may further comprise the step of assaying the sample for methylation status of a gene selected from the group consisting of NPY, JAM2, MAL, LAMA1, SLIT2, RERG, and a combination thereof. In some cases, the methylation status of one or more of P15.INK4b, somatostatin, GAS7, CNRIP1, and PIK3CG or any other gene identified herein is compared to a standard. In specific embodiments, the standard is a methylation threshold value from a normal sample.

Some methods of the invention further comprise the step of assaying the sample for methylation status of a gene selected from the group consisting of ADHFE1, COL1A2, EPHA7, RUNX3, MDR1, CHFR, N33.TUMOR_SUPPRESSOR_CANDIDATE_3, RASSF2, DAB21P, HPP1, SFRP1, CXX1, ESTROGEN_RECEPTOR_1, FAS, DSC3, MUC2, RETINOIC_RECEPTOR_ACID_BETA_2, and a combination thereof. Some methods of the invention further comprise the step of assaying the sample for methylation status of a gene selected from the group consisting of ADHFE1, COL1A2, EPHA7, RUNX3, MDR1, CHFR, N33.TUMOR_SUPPRESSOR_CANDIDATE_3, RASSF2, DAB21P, HPP1, SFRP1, CXX1, ESTROGEN_RECEPTOR_1, FAS, DSC3, MUC2, RETINOIC_RECEPTOR_ACID_BETA_2, and a combination thereof.

Certain methods of the invention further comprise the step of assaying the sample for methylation status of a gene selected from the group consisting of NPY, JAM2, MAL, LAMA1, SLIT2, and a combination thereof.

For certain embodiments of the present invention, the method is performed as part of a regular checkup. Therefore, for these methods the subject has not been diagnosed with cancer, and typically for those particular embodiments it is not known that a subject has a hyperproliferative disorder, such as a colorectal neoplasm. In other embodiments the individual is at risk for colorectal cancer, is suspected of having colorectal cancer, or has a personal or family history of cancer, including colorectal cancer, for example. In some cases, an individual is known to have cancer and undergoes methods of the invention to determine the type of CRC, staging of CRC, treatment response to CRC, and/or prognosis. In other cases, the individual has already been diagnosed for CRC cancer and may be subjected to surgery for CRC cancer resection and may undergo methods of the invention to survey the recurrence of polyps or CRC cancer.

In alternative embodiments of the invention, the gene expression level of one or more of the genes listed herein is indicative of colorectal cancer diagnosis, screening, and/or prognosis, and the expression may be determined at the mRNA or protein level by routine methods in the art. In some alternative embodiments, cancers other than colorectal may be identified or prognosticated with methods and/or compositions of the invention, such as lung, breast, prostate, pancreas, liver, spleen, bone, blood, ovary, testis, brain, gall bladder, kidney, bladder, skin, and so forth.

In some embodiments, there is a method of treating an individual for colorectal cancer, comprising the step of providing to the individual one or more suitable therapies for colorectal cancer when the individual has a methylation status of one or more certain genes (or at least two, at least three, at least four, or all of P15.INK4b, somatostatin, GAS7, CNRIP1, and PIK3CG) that is indicative of the presence of colorectal cancer. Exemplary treatments for colorectal cancer include local excision or simple polypectomy; resection and/or anastomosis; radiation; chemotherapy (Adrucil, Avastin, Bevacizumab, Camptosar, Cetuximab, Efudex, Erbitux, Fluoroplex, Fluorouracil, Irinotecan Hydrochloride, Panitumumab, Regorafenib, Stivarga, Vectibix, Zaltrap, and/or Ziv-Aftibercept); gene therapy including gene therapy that modifies methylation status of a gene; and/or targeted therapy with monoclonal antibodies. In some embodiments of the invention, the method encompasses the step of analyzing the methylation status of one or more of P15.INK4b, somatostatin, GAS7, CNRIP1, and PIK3CG.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which:

FIG. 1 shows exemplary combinations of biomarkers with 100% of specificity assessed in 32 patients with adenomas versus 32 normal patients. Grey squares: The serum predicted methylation value is above 33% of the difference between the full methylation state and the highest methylation value in the set of 32 normal subjects (threshold gene-specific). White (W) squares: The serum predicted methylation value is under the gene-specific threshold. Vimentin as an exemplary known behavior was used as a reference.

DESCRIPTION OF THE INVENTION

As used herein the specification, "a" or "an" may mean one or more. As used herein in the claim(s), when used in conjunction with the word "comprising", the words "a" or "an" may mean one or more than one. As used herein "another" may mean at least a second or more. In specific embodiments, aspects of the invention may "consist essentially of" or "consist of" one or more sequences of the invention, for example. Some embodiments of the invention may consist of or consist essentially of one or more elements, method steps, and/or methods of the invention. It is contemplated that any method or composition described herein can be implemented with respect to any other method or composition described herein. Embodiments discussed in the context of methods and/or compositions of the invention may be employed with respect to any other method or composition described herein. Thus, an embodiment pertaining to one method or composition may be applied to other methods and compositions of the invention as well.

As used in this application, the terms "about" and "approximately" are used as equivalents. Any numerals used in this application with or without about/approximately are meant to cover any normal fluctuations appreciated by one of ordinary skill in the relevant art.

The present invention will help for non-invasive tumour diagnosis at early stage of CRC patients. It will contribute to increasing the overall survival of CRC patients and will contribute to significantly reduce the cost of patients supported by health authorities. Moreover, the invention will be easy for routine clinical use by any medical testing/pathology laboratory.

Determine: Many methodologies described herein may include a step of "determining". Those of ordinary skill in the art, reading the present specification, will appreciate that such "determining" can utilize any of a variety of techniques available to those skilled in the art, including for example specific techniques explicitly referred to herein. In some embodiments, a determination involves manipulation of a physical sample. In some embodiments, a determination involves consideration and/or manipulation of data or information, for example utilizing a computer or other processing unit adapted to perform a relevant analysis. In some embodiments, a determination involves receiving relevant information and/or materials from a source.

Isolated: The term "isolated", as used herein, refers to an agent or entity that has either (i) been separated from at least some of the components with which it was associated when initially produced (whether in nature or in an experimental setting); or (ii) produced by the hand of man. Isolated agents or entities may be separated from at least about 10%, at least about 20%, at least about 30%, at least about 40%, at least about 50%, at least about 60%, at least about 70%, at least about 80%, at least about 90%, or more of the other components with which they were initially associated. In some embodiments, isolated agents are more than 90%, 91%, 92%, 93%, 94%, 95%, 96%, 97%, 98%, 99% pure.

Nucleic acid molecule: The term "nucleic acid molecule" is used broadly to mean any polymer of two or more nucleotides, which are linked by a covalent bond such as a phosphodiester bond, a thioester bond, or any of various other bonds known in the art as useful and effective for linking nucleotides. Such nucleic acid molecules can be linear, circular or supercoiled, and can be single stranded or double stranded, e.g. single stranded or double stranded DNA, RNA or DNA/RNA hybrid. In some embodiments, nucleic acid molecules are or include nucleic acid analogs that are less susceptible to degradation by nucleases than are DNA and/or RNA. For example, RNA molecules containing 2'-O-methylpurine substitutions on the ribose residues and short phosphorothioate caps at the 3'- and 5'-ends exhibit enhanced resistance to nucleases (Green et al., Chem. Biol., 2:683-695 (1995), which is incorporated herein by reference). Similarly, RNA containing 2'-amino-2'-deoxypyrimidines or 2'-fluoro-2'-deoxypyrimidines is less susceptible to nuclease activity (Pagratis et al., Nature Biotechnol., 15:68-73 (1997), which is incorporated herein by reference). Furthermore, L-RNA, which is a stereoisomer of naturally occurring D-RNA, is resistant to nuclease activity (Nolte et al., Nature Biotechnol., 14:1116-1119 (1996); Klobmann et al., Nature Biotechnol., 14:1112-1115 (1996); each of which is incorporated herein by reference). Such RNA molecules and methods of producing them are well known in the art and can be considered to be routine (see Eaton and Piekern, Ann. Rev. Biochem., 64:837-863 (1995), which is incorporated herein by reference). DNA molecules containing phosphorothioate linked oligodeoxynucleotides are nuclease resistant (Reed et al., Cancer Res. 50:6565-6570 (1990), which is incorporated herein by reference). Phosphorothioate-3' hydroxypropylamine modification of the phosphodiester bond also reduces the susceptibility of a DNA molecule to nuclease degradation (see Tam et al., Nucl. Acids Res., 22:977-986 (1994), which is incorporated herein by reference).

Organ or Tissue: As used herein, the terms "organ or tissue" and "selected organ or tissue" are used in the broadest sense to mean an organ or tissue in or from a body. In some embodiments, an organ or tissue has a pathology, for example, tissue containing tumors (including lung containing tumors), whether primary or metastatic lesions. In some embodiments, an organ or tissue is normal (e.g., healthy). The term "control organ or tissue" is used to mean an organ or tissue other than a selected organ or tissue of interest. In some embodiments, a control organ or tissue is characterized by the inability of a ligand-encoding phage to home to the control organ or tissue and, therefore, is useful for identifying selective binding of a molecule to a selected organ or tissue.

Sample: As used herein, the term "sample" refers to a cell, tissue, organ or portion thereof that is isolated from a body. It will be appreciated that a sample may be or comprise a single cell or a plurality of cells. In some embodiments, a sample is or comprises a histologic section or a specimen obtained by biopsy (e.g., surgical biopsy); in some embodiments, a sample is or comprises cells that are or have been placed in or adapted to tissue culture. In some embodiments, the sample is or comprises an intact organ or tissue. In some embodiments, the sample is or comprises circulating cells, such as circulating tumor cells. In some embodiments a sample is obtained by an individual that is performing the methylation assay, whereas in some embodiments a sample is obtained by an individual that is not performing the methylation assay. The obtaining of the sample encompasses extracting the sample itself from the individual being tested yet also encompasses retrieving the sample from its transmittal or from storage, either directly or indirectly. The sample may be from or be representative of a sample from the colon and/or rectum Sample processing: As used herein, the term "sample processing" generally refers to various steps that may be accomplished to prepare a sample for quantification. In some embodiments, crude sample (e.g., whole tissue, homogenized tissue, etc.) is prepared. In some embodiments, purified or highly purified sample is prepared.

Subject: As used herein, the terms "subject," "individual" or "patient" refer to a human or a non-human mammalian subject. In some embodiments, a subject is a non-human primate. In some embodiments, the subject is a dog, cat, goat, horse, pig, mouse, rabbit, or the like. In some embodiments, a subject is a human. In some embodiments, a subject is healthy. In some embodiments, a subject is suffering from or susceptible to a disease, disorder or condition (e.g., associated with the endothelium). In some embodiments, a human subject is a patient having a surgical tumor resection or a surgical biopsy. In some embodiments, a human subject is overweight, obese, has a metabolic condition related to being overweight or obese, or has cancer, is suspected of having cancer, or is at risk for developing cancer.

I. General Embodiments of the Invention

In some embodiments of the invention, there are methods and compositions suitable for CRC screening, diagnosis, and/or prognosis. The embodiments include certain markers that are assayed to determine the presence or absence of CRC, the type of CRC, the stage of CRC, the response to treatment for CRC, the prognosis with CRC, and so forth. Although all of the genes listed herein may be included for the determination, in some embodiments less than all of the genes are employed.

The present combinations of the biomarkers proposed in this invention are unique for the diagnosis and/or prognosis of CRC patients. All or part of the provided markers may be used for colorectal screening, and in particular aspects, the methylation of any region of the gene is considered. In specific embodiments, however, the methylation of one or more regulatory regions may be considered for each gene in question (these include but are not restricted to the promoter, first exon, enhancers, silencers, and other regulatory regions). In cases where less than the listed 29 specific genes are employed for diagnosis, there may be 28 or less, 27 or less, 26 or less, 25 or less, 24 or less, 23 or less, 22 or less, 21 or less, 20 or less, 19 or less, 18 or less, 17 or less, 16 or less, 15 or less, 14 or less, 13 or less, 12 or less, 11 or less, 10 or less, 9 or less, 8 or less, 7 or less, 6 or less, 5 or less, 4 or less, or 3 or less. The assaying may be employed as part of routine screening of a patient or may be employed upon indication that an individual either has or is at risk for having colorectal cancer or is in need of prognosis, response to treatment, recurrence survey, typing or staging of CRC.

II. Individuals for Screening

An individual subjected to methods and compositions of the invention may be of any kind, so long as it is desired to know whether or not the individual has or is at risk for or is in need of prognosis, response to treatment, typing or staging of CRC. In some embodiments, the individual is at least 50, 55, 60, 65, or 70 years or older in age, although in some cases the individual is less than 50 years old and may or may not have family or personal history and/or symptoms. The individual may have one or more symptoms of colorectal cancer or may be asymptomatic for colorectal cancer. In some cases, the individual has a prior history of having cancer, including a prior history of having colorectal cancer.

In cases wherein an individual has one or more symptoms of a colorectal medical disorder, the individual may be subjected to methods or compositions of the invention. In specific cases, the individual has one or more symptoms selected from the group consisting of a change in bowel habits, constipation that lasts more than a couple of weeks, diarrhea that lasts more than a couple of weeks, a feeling that the bowel does not empty completely, blood in the stool, narrow or thinner than normal stool, abdominal discomfort, gas pains, bloating, fullness, cramps, weight loss, fatigue, anemia, and a combination thereof.

A person who is at risk for developing colorectal cancer may be an individual that is over 50 years in age and/or has a personal or family history of colorectal cancer and/or has or has had colon polyps, and/or are positive for hemmocult test and/or had surgery for CRC and/or has low fiber diet and/or high fat diet and/or is a tobacco user and/or suffered from inflammatory bowel disease(s). In cases where the individual has had a person or family history, the individual may have a personal or family history of familial adenomatous polyposis, Lynch syndrome, Peutz-Jeghers syndrome or juvenile polyposis syndrome, for example.

In some cases of the invention, the individual is subjected to one or more other assays for determination of colorectal cancer. Although any other assay may be employed, in some cases the one or more other assays is selected from the group consisting of stool testing, barium enema, virtual colonoscopy, sigmoidoscopy, carcinoembryonic antigen (CEA) tests, KRAS tests, microsatellites deficiency tests, and colonoscopy.

In cases where the individual has been identified as having cancer the colorectal cancer may originate in the colon or rectum of the individual (or may be a primary cancer that metastasizes to the colon and/or rectum). In some cases, when the individual is determined to have cancer, the individual has stage 0, 1, 2, 3, or 4 colorectal cancer.

Any type of colorectal cancer may be encompassed with methods and compositions of the invention, including polyps, adenoma less than 1 cm, adenoma more than 1 cm, adenocarcinomas, and also all microsatellites proficient and microsatellites deficient cancer types.

III. Measuring Methylation Patterning

In embodiments of the invention, the methylation pattern of one or more genes is determined for diagnosis, screening, and/or prognosticating colorectal cancer in an individual. In particular aspects of the invention, the methylation patterning measurements are quantifiable. The methylation may be determined over the sequence overlapping a gene and gene regulatory regions not overlapping the gene (e.g. enhancers, silencers, distal promoters, etc.). A skilled artisan recognizes that the boundaries genes may be obtained from any gene bank database with well annotated genes, such as the National Center for Biotechnology Information's database, the EMBL Nucleotide Sequence Database (also known as EMBL-Bank) and the UCSC Genome Browser.

The methylation pattern may be determined by any suitable means in the art, although in specific embodiments the methylation pattern is determined with methylation-specific PCR (including probe-based real-time PCR for methylation analysis; see, for example, Herman et al., 1996; Goel et al., 2004; Ishiguro et al., 2006)(such as methylight PCR (Qiagen; Valencia, Calif., Applied Biosystems, Roche diagnostics)); methylation array (Illumina, Agilent, Affymetrix); methylation sequencing (including bisulfate DNA sequencing; see Dallol et al., 2003; and Oster et al., 2011; Kim et al., 2011, for example); methyl-beaming (Nature Biotechnol. 2009, September; 27(9): 858-863 for example); mass spectrometry; a combination thereof; and so forth. In some methods, quantity of DNA is required for comparison, and there are standard means in the art for this, including spectrophotometry and/or gel electrophoresis, for example. Thus, numerous methods for analyzing methylation status of a gene are known in the art and can be used in the methods of the present invention to identify methylation status of a gene.

In specific embodiments, part of analysis of methylation includes bisulfite genomic sequencing. Accordingly, denatured genomic DNA can be treated with freshly prepared bisulfite solution at 55° C. in the dark overnight (or only incubation for 3 hours), followed by column purification and NaOH treatment, for example. Bisulfite treatment modifies DNA converting unmethylated, but not methylated, cytosines to uracil.

In some embodiments, methylation assays allow for determination of the methylation state of one or a plurality of CpG dinucleotides (e.g., CpG islands) within a DNA sequence. Such assays involve, among other techniques, DNA sequencing of bisulfite-treated DNA, PCR (for sequence-specific amplification), Southern blot analysis, use of methylation-sensitive restriction enzymes, etc. For example, genomic sequencing has been simplified for analysis of DNA methylation patterns and 5-methylcytosine distribution by using bisulfite treatment (Frommer et al., Proc. Natl. Acad. Sci. USA 89:1827-1831, 1992). Additionally, restriction enzyme digestion of PCR products amplified from bisulfite-converted DNA is used, e.g., the method described by Sadri and Hornsby (Nucl. Acids Res. 24:5058-5059, 1996), or Combined Bisulfite Restriction Analysis (COBRA) (Xiong and Laird, Nucleic Acids Res. 25:2532-2534, 1997).

Combinations of methods for quantifying methylation may be employed.

A. Cobra

COBRA analysis is a quantitative methylation assay useful for determining DNA methylation levels at specific gene loci in small amounts of genomic DNA (Xiong and Laird, Nucleic Acids Res. 25:2532-2534, 1997). Briefly, restriction enzyme digestion is used to reveal methylation-dependent sequence differences in PCR products of sodium bisulfite-treated DNA. Methylation-dependent sequence differences are first introduced into the genomic DNA by standard bisulfite treatment according to the procedure described by Frommer et al. (Proc. Natl. Acad. Sci. USA 89:1827-1831, 1992). PCR amplification of the bisulfite converted DNA is then performed using primers specific for the interested CpG islands, followed by restriction endonuclease digestion, gel electrophoresis, and detection using specific, labeled hybridization probes. Methylation levels in the original DNA sample are represented by the relative amounts of digested and undigested PCR product in a linearly quantitative fashion across a wide spectrum of DNA methylation levels. In addition, this technique can be reliably applied to DNA obtained from microdissected paraffin-embedded tissue samples or body fluids circulating DNA. Typical reagents (e.g., as might be found in a typical COBRA-based kit) for COBRA analysis may include, but are not limited to: PCR primers for specific gene (or methylation-altered DNA sequence or CpG island); restriction enzyme and appropriate buffer; gene-hybridization oligo; control hybridization oligo; kinase labeling kit for oligo probe; and radioactive nucleotides. Additionally, bisulfite conversion reagents may include: DNA denaturation buffer; sulfonation buffer; DNA recovery regents or kit (e.g., precipitation, ultrafiltration, affinity column); desulfonation buffer; and DNA recovery components.

B. MethyLight

The MethyLight assay is a high-throughput quantitative methylation assay that utilizes fluorescence-based real-time PCR (TaqMan®) technology that requires no further manipulations after the PCR step (Eads et al., Cancer Res. 59:2302-2306, 1999). Briefly, the MethyLight process begins with a mixed sample of genomic DNA that is converted, in a sodium bisulfite reaction, to a mixed pool of methylation-dependent sequence differences according to standard procedures (the bisulfite process converts unmethylated cytosine residues to uracil). Fluorescence-based PCR is then performed either in an "unbiased" (with primers that do not overlap known CpG methylation sites) PCR reaction, or in a "biased" (with PCR primers that overlap known CpG dinucleotides) reaction. Sequence discrimination can occur either at the level of the amplification process or at the level of the fluorescence detection process, or both.

The MethyLight may assay be used as a quantitative test for methylation patterns in the genomic DNA sample, wherein sequence discrimination occurs at the level of probe hybridization. In this quantitative version, the PCR reaction provides for unbiased amplification in the presence of a fluorescent probe that overlaps a particular putative methylation site. An unbiased control for the amount of input DNA is provided by a reaction in which neither the primers, nor the probe overlie any CpG dinucleotides. Alternatively, a qualitative test for genomic methylation is achieved by probing of the biased PCR pool with either control oligonucleotides that do not "cover" known methylation sites (a fluorescence-based version of the "MSP" technique), or with oligonucleotides covering potential methylation sites.

The MethyLight process can by used with a "TaqMan®" probe in the amplification process. For example, double-stranded genomic DNA is treated with sodium bisulfite and subjected to one of two sets of PCR reactions using TaqMan® probes; e.g., with either biased primers and TaqMan® probe, or unbiased primers and TaqMan® probe. The TaqMan® probe is dual-labeled with fluorescent "reporter" and "quencher" molecules, and is designed to be specific for a relatively high GC content region so that it melts out at about 10° C. higher temperature in the PCR cycle than the forward or reverse primers. This allows the TaqMan® probe to remain fully hybridized during the PCR annealing/extension step. As the Taq polymerase enzymatically synthesizes a new strand during PCR, it will eventually reach the annealed TaqMan® probe. The Taq polymerase 5' to 3' endonuclease activity will then displace the TaqMan® probe by digesting it to release the fluorescent reporter molecule for quantitative detection of its now unquenched signal using a real-time fluorescent detection system.

Typical reagents (e.g., as might be found in a typical MethyLight-based kit) for MethyLight analysis may include, but are not limited to: PCR primers for specific gene (or methylation-altered DNA sequence or CpG island); TaqMan® probes; optimized PCR buffers and deoxynucleotides; and Taq polymerase.

C. Ms-SNuPE

The Ms-SNuPE technique is a quantitative method for assessing methylation differences at specific CpG sites based on bisulfite treatment of DNA, followed by single-nucleotide primer extension (Gonzalgo and Jones, Nucleic Acids Res. 25:2529-2531, 1997). Briefly, genomic DNA is reacted with sodium bisulfite to convert unmethylated cytosine to uracil while leaving 5-methylcytosine unchanged. Amplification of the desired target sequence is then performed using PCR primers specific for bisulfite-converted DNA, and the resulting product is isolated and used as a template for methylation analysis at the CpG site(s) of interest. Small amounts of DNA can be analyzed (e.g., microdissected pathology sections), and it avoids utilization of restriction enzymes for determining the methylation status at CpG sites. Typical reagents (e.g., as might be found in a typical Ms-SNuPE-based kit) for Ms-SNuPE analysis may include, but are not limited to: PCR primers for specific gene (or methylation-altered DNA sequence or CpG island); optimized PCR buffers and deoxynucleotides; gel extraction kit; positive control primers; Ms-SNuPE primers for specific gene; reaction buffer (for the Ms-SNuPE reaction); and radioactive nucleotides. Additionally, bisulfite conversion reagents may include: DNA denaturation buffer; sulfonation buffer; DNA recovery regents or kit (e.g., precipitation, ultrafiltration, affinity column); desulfonation buffer; and DNA recovery components.

D. Methylated CpG Island Amplification (MCA)

The MCA technique is a method that can be used to screen for altered methylation patterns in genomic DNA, and to isolate specific sequences associated with these changes (Toyota et al., Cancer Res. 59:2307-12, 1999). Briefly, restriction enzymes with different sensitivities to cytosine methylation in their recognition sites are used to digest genomic DNAs from primary tumors, cell lines, and normal tissues prior to arbitrarily primed PCR amplification. Fragments that show differential methylation are cloned and sequenced after resolving the PCR products on high-resolution polyacrylamide gels. The cloned fragments are then used as probes for Southern analysis to confirm differential methylation of these regions. Typical reagents (e.g., as might be found in a typical MCA-based kit) for MCA analysis may include, but are not limited to: PCR primers for arbitrary priming Genomic DNA; PCR buffers and nucleotides, restriction enzymes and appropriate buffers; gene-hybridization oligos or probes; control hybridization oligos or probes.

E. Methyl-BEAMing:

In BEAMing, PCR amplification of individual DNA molecules takes place within aqueous nanocompartments suspended in a continuous oil phase. Each aqueous nanocompartment contains the DNA polymerase, cofactors, and dNTP's required for PCR. When a compartment contains a single DNA template molecule as well as a bead, the PCR product within the compartment becomes bound to the bead. Each bead thereby ends up with thousands of identical copies of the template within its nano-compartment a process similar to that resulting from cloning an individual DNA fragment into a plasmid vector to form a bacterial colony. After PCR, the beads are collected by breaking the emulsion, and their status is individually assessed by incubation with fluorescent hybridization probes. In Methyl-BEAMing, the status of harvested beads is interrogated by fluorescent probes that specifically hybridize to either methylated or unmethylated derived sequences, with flow cytometry providing an accurate enumeration of the fraction of original template molecules that were methylated or unmethylated within the queried sequence (Nature Biotecnol 2009 September; 27(9):858-863).

F. Methylation Specific Polymerase Chain Reaction (MSP)

In one embodiment, the invention provides a method for detecting a methylated CpG-containing nucleic acid, the method including contacting a nucleic acid-containing specimen with an agent that modifies unmethylated cytosine; amplifying the CpG-containing nucleic acid in the specimen by means of CpG-specific oligonucleotide primers; and detecting the methylated nucleic acid. It is understood that while the amplification step is optional, it is desirable in the preferred method of the invention.

The term "modifies" as used herein means the conversion of an unmethylated cytosine to another nucleotide that will distinguish the unmethylated from the methylated cytosine. Preferably, the agent modifies unmethylated cytosine to uracil. Preferably, the agent used for modifying unmethylated cytosine is sodium bisulfite, however, other agents that similarly modify unmethylated cytosine, but not methylated cytosine can also be used in the method of the invention or any method allowing the distinguishing between the methylated cytosine and the unmethylated cytosine. Sodium bisulfite ($NaHSO_3$) reacts readily with the 5,6-double bond of cytosine, but poorly with methylated cytosine. Cytosine reacts with the bisulfite ion to form a sulfonated cytosine reaction intermediate which is susceptible to deamination, giving rise to a sulfonated uracil. The sulfonate group can be removed under alkaline conditions, resulting in the formation of uracil. Uracil is recognized as a thymine by Taq polymerase and therefore upon PCR, the resultant product contains cytosine only at the position where 5-methylcytosine occurs in the starting template DNA.

The primers used in the invention for amplification of the CpG-containing nucleic acid in the specimen, after bisulfite modification, specifically distinguish between methylated and non-methylated DNA, in particular embodiments of the invention. Two exemplary types of primers could be designed: one set recognizing methylated cytosine and the other set targeting the unmethylated cytosine. The first set of primers enables one to assess the methylation; however, the second set enables one to quantify the unmethylated DNA. MSP primers for the non-methylated DNA preferably have a T in the 3' CG pair to distinguish it from the C retained in methylated DNA, and the compliment is designed for the antisense primer. MSP primers usually contain relatively few Cs or Gs in the sequence since the Cs will be absent in the sense primer and the Gs absent in the antisense primer (C becomes modified to U (uracil) which is amplified as T (thymidine) in the amplification product).

The primers of the invention embrace oligonucleotides of sufficient length and appropriate sequence so as to provide specific initiation of polymerization on a significant number of nucleic acids in the polymorphic locus. Specifically, the term "primer" as used herein refers to a sequence comprising two or more deoxyribonucleotides or ribonucleotides, preferably more than three, and most preferably more than 8, which sequence is capable of initiating synthesis of a primer extension product, which is substantially complementary to a polymorphic locus strand. Environmental conditions conducive to synthesis include the presence of nucleoside triphosphates and an agent for polymerization, such as DNA polymerase, and a suitable temperature and pH. The primer is preferably single stranded for maximum efficiency in amplification, but may be double stranded. If double stranded, the primer is first treated to separate its strands before being used to prepare extension products. Preferably, the primer is an oligodeoxy ribonucleotide. The primer must be sufficiently long to prime the synthesis of extension products in the presence of the inducing agent for polymerization. The exact length of primer will depend on many factors, including temperature, buffer, and nucleotide composition. The oligonucleotide primer typically contains 12-20 or more nucleotides, although it may contain fewer nucleotides.

Primers of the invention are designed to be "substantially" complementary to each strand of the genomic locus to be amplified and include the appropriate G or C nucleotides as discussed above. This means that the primers must be sufficiently complementary to hybridize with their respective strands under conditions which allow the agent for polymerization to perform. In other words, the primers should have sufficient complementarity with the 5' and 3' flanking sequences to hybridize therewith and permit amplification of the genomic locus.

Oligonucleotide primers of the invention are employed in the amplification process which is an enzymatic chain reaction that produces exponential quantities of target locus relative to the number of reaction steps involved. Typically, one primer is complementary to the negative (−) strand of the locus and the other is complementary to the positive (+) strand. Annealing the primers to denatured nucleic acid followed by extension with an enzyme, such as the large fragment of DNA Polymerase I and nucleotides, results in newly synthesized + and − strands containing the target locus sequence. Because these newly synthesized sequences are also templates, repeated cycles of denaturing, primer annealing, and extension results in exponential production of the region (i.e., the target locus sequence) defined by the primer. The product of the chain reaction is a discrete nucleic acid duplex with termini corresponding to the ends of the specific primers employed.

The oligonucleotide primers of the invention may be prepared using any suitable method, such as conventional phosphotriester and phosphodiester methods or automated embodiments thereof. In one such automated embodiment, diethylphosphoramidites are used as starting materials and may be synthesized as described by Beaucage, et al. (Tetrahedron Letters, 22:1859-1862, 1981). One method for synthesizing oligonucleotides on a modified solid support is described in U.S. Pat. No. 4,458,066.

Any nucleic acid specimen, in purified or nonpurified form, can be utilized as the starting nucleic acid or acids, provided it contains, or is suspected of containing, the specific nucleic acid sequence containing the target locus (e.g., CpG). Thus, the process may employ, for example, DNA or RNA, including messenger RNA, wherein DNA or RNA may be single stranded or double stranded. In the event that RNA is to be used as a template, enzymes, and/or conditions optimal for reverse transcribing the template to DNA would be utilized. In addition, a DNA-RNA hybrid which contains one strand of each may be utilized. A mixture of nucleic acids may also be employed, or the nucleic acids produced in a previous amplification reaction herein, using the same or different primers may be so utilized. The specific nucleic acid sequence to be amplified, i.e., the target locus, may be a fraction of a larger molecule or can be present initially as a discrete molecule, so that the specific sequence constitutes the entire nucleic acid. It is not necessary that the sequence to be amplified be present initially in a pure form; it may be a minor fraction of a complex mixture, such as contained in whole human DNA.

The nucleic acid-containing specimen used for detection of methylated CpG may be from any source including brain, colon, urogenital, hematopoietic, thymus, testis, ovarian, uterine, prostate, breast, colon, lung and renal tissue and may be extracted by a variety of techniques such as that described by Maniatis, et al. (Molecular Cloning: A Laboratory Manual, Cold Spring Harbor, N.Y., pp 280, 281, 1982).

If the extracted sample is impure (such as plasma, serum, or blood or a sample embedded in parrafin), it may be treated before amplification with an amount of a reagent effective to open the cells, fluids, tissues, or animal cell membranes of the sample, and to expose and/or separate the strand(s) of the nucleic acid(s). This lysing and nucleic acid denaturing step to expose and separate the strands will allow amplification to occur much more readily.

Where the target nucleic acid sequence of the sample contains two strands, it is necessary to separate the strands of the nucleic acid before it can be used as the template. Strand separation can be effected either as a separate step or simultaneously with the synthesis of the primer extension products. This strand separation can be accomplished using various suitable denaturing conditions, including physical, chemical, or enzymatic means, the word "denaturing" includes all such means. One physical method of separating nucleic acid strands involves heating the nucleic acid until it is denatured. Typical heat denaturation may involve temperatures ranging from about 80° to 105° C. for times ranging from about 15 seconds to 10 minutes. Strand separation may also be induced by an enzyme from the class of enzymes known as helicases or by the enzyme RecA, which has helicase activity, and in the presence of riboATP, is known to denature DNA. The reaction conditions suitable for strand separation of nucleic acids with helicases are described by Kuhn Hoffmann-Berling (CSH-Quantitative Biology, 43:63, 1978) and techniques for using RecA are reviewed in C. Radding (Ann. Rev. Genetics, 16:405-437, 1982).

When complementary strands of nucleic acid or acids are separated, regardless of whether the nucleic acid was originally double or single stranded, the separated strands are ready to be used as a template for the synthesis of additional nucleic acid strands. This synthesis is performed under conditions allowing hybridization of primers to templates to occur. Generally synthesis occurs in a buffered aqueous solution, preferably at a pH of 7-9, most preferably about 8. Preferably, a molar excess (for genomic nucleic acid, usually about $10^8$:1 primer:template) of the two oligonucleotide primers is added to the buffer containing the separated template strands. It is understood, however, that the amount of complementary strand may not be known if the process of the invention is used for diagnostic applications, so that the amount of primer relative to the amount of complementary strand cannot be determined with certainty. As a practical matter, however, the amount of primer added will generally be in molar excess over the amount of complementary strand (template) when the sequence to be amplified is contained in a mixture of complicated long-chain nucleic acid strands. A large molar excess is preferred to improve the efficiency of the process.

The deoxyribonucleoside triphosphates dATP, dCTP, dGTP, and dTTP are added to the synthesis mixture, either separately or together with the primers, in adequate amounts and the resulting solution is heated to about 90°-100° C. from about 15 seconds to 10 minutes, preferably from 1 to 4 minutes. After this heating period, the solution is allowed to cool to hybridization temperature primers specific $T_m$, which is preferable for the primer hybridization. To the mixture is added an appropriate agent for effecting the primer extension reaction (called herein "agent for polymerization"), and the reaction is allowed to occur under conditions known in the art. The agent for polymerization may also be added together with the other reagents if it is heat stable. This synthesis (or amplification) reaction may occur at $T_m$ temperature up to a temperature above which the agent for polymerization no longer functions.

The agent for polymerization may be any compound or system which will function to accomplish the synthesis of primer extension products, including enzymes. Suitable enzymes for this purpose include, for example, *E. coli* DNA polymerase I, Klenow fragment of *E. coli* DNA polymerase I, T4 DNA polymerase, other available DNA polymerases, polymerase muteins, reverse transcriptase, and other enzymes, including heat-stable enzymes (i.e., those enzymes which perform primer extension after being subjected to temperatures sufficiently elevated to cause denaturation). Suitable enzymes will facilitate combination of the nucleotides in the proper manner to form the primer extension products which are complementary to each locus nucleic acid strand. Generally, the synthesis will be initiated at the 3' end of each primer and proceed in the 5' direction along the template strand, until synthesis terminates, producing molecules of different lengths. There may be agents for polymerization, however, which initiate synthesis at the 5' end and proceed in the other direction, using the same process as described above.

Preferably, the method of amplifying is by PCR, as described herein and as is commonly used by those of ordinary skill in the art. Alternative methods of amplification have been described and can also be employed as long as the methylated and non-methylated loci amplified by PCR using the primers of the invention is similarly amplified by the alternative means.

The amplified products are preferably identified as methylated or non-methylated by sequencing. Sequences amplified by the methods of the invention can be further evaluated, detected, cloned, sequenced, and the like, either in solution or after binding to a solid support, by any method usually applied to the detection of a specific DNA sequence such as PCR, oligomer restriction (Saiki, et al., Bio/Technology, 3:1008-1012, 1985), allele-specific oligonucleotide (ASO) probe analysis (Conner, et al., Proc. Natl. Acad. Sci. USA, 80:278, 1983), oligonucleotide ligation assays (OLAs) (Landegren, et al., Science, 241:1077, 1988), and the like. Molecular techniques for DNA analysis have been reviewed (Landegren, et al., Science, 242:229-237, 1988).

Optionally, the methylation pattern of the nucleic acid can be confirmed by restriction enzyme digestion and Southern blot analysis. Examples of methylation sensitive restriction endonucleases which can be used to detect 5'CpG methylation include SmaI, SacII, EagI, MspI, HpaII, BstUI and BssHII, for example.

The amplified products may be identified as methylated or unmethylated by sequencing, using capillary sequencing, for example (briefly, the treated amplified DNA is amplified by either forward or reverse primers in the presence of dideoxyribonucleotides that stop the sequencing reaction and subjected to capillary electrophoresis to read the target sequence), using high-throughput sequencing (sequencing by synthesis (Applied Biosystems), by pyrosequencing (454 Roche diagnostics) or by others technologies such as Illumina, Pacific Bio and Helicos.

IV. Exemplary Determination of Methylation Values

In embodiments of the invention, identification of methylation parameters of any kind for one or more particular genes allows screening, diagnosing, and/or prognosticating colorectal cancer in an individual. In some cases, quantification of methylation of one or more regions of one or more particular genes allows screening, diagnosing, and/or prognosticating colorectal cancer in an individual. The region may be of any kind in the gene so long as it is able to be methylated, but in specific cases the region comprises CpG island(s).

In certain aspects of the invention, there is measuring of methylation in a relative or absolute way for each patient, marker and sample type (e.g., serum, urine, and so forth). In exemplary embodiments, methylation is measured by any of the above-referenced exemplary methods. The results of such an exemplary measurement may be provided as a percent ranging from 0% (no methylation) to 100% (full methylation, in an absolute way). In some cases, there is a specific value that can be compared to normal subjects' (subjects cancer free, for example in the same age range) values (in a relative way), for example.

In specific aspects to the invention, markers that are hypermethylated in cancer are utilized, for example, given that markers in individuals without cancer will be less methylated than in individuals with cancer. In alternative embodiments, markers that are hypomethylated are utilized in comparison to normals with higher methylation.

A threshold for methylation for a particular gene may be determined, in some embodiments. In some embodiments of the invention for a given individual, marker, and/or sample type, one can observe the methylation values in the cancer-free population (referred to as normals) and one can take the maximum of those values as a threshold (referred to as Th) against which non-cancer and cancer individuals can be distinguished. As an example only, in the case of P15INK4 in serum, the data from cancer vs. cancer-free studies that was used showed 59% as the highest methylation value for the cancer-free individuals. Therefore, in this particular case, Th=59%.

In specific embodiments, for a given sample type the Th is different from marker to marker. For example, those Th that the inventors utilized for serum are derived from 64 individuals (32 cancer and 32 cancer free). In large cohort studies this Th may vary. In some cases, when a larger population is assayed, the value for Th by observing available data may be expected to be lower than the value in the actual population, and the skilled artisan recognizes to take this into consideration whether or not to employ a particular marker to distinguish between cancer and non-cancer. However, for particularly useful markers the cancer/non-cancer distinction remains very good even when the threshold is increased. This is apparent when studying the test's accuracy at higher thresholds.

The following example illustrates how this increased threshold in practice can be determined, again using the exemplary case of P15INK4 in serum.

Th=59% in this case. To compensate for possibly lower estimates of the threshold because of a smaller population group, the inventors increased Th by (for example) 5%, 10%, 20%, 25%, 33% of the difference between the full methylation (100%) and Th. The calculations are shown as follows:

$$Th1=59\%+(100-59)*0.05=59\%+2.05\%$$

$$Th2=59\%+(100-59)*0.10=59\%+4.1\%$$

$$Th3=59\%+(100-59)*0.20=59\%+8.2\%$$

$$Th4=59\%+(100-59)*0.25=59\%+10.25\%$$

$$Th5=59\%+(100-59)*0.33=59\%+13.53\%$$

So, one can see the increase in threshold that can be used to distinguish cancer vs. non-cancer cases. This for itself determines which genes serve as markers under such specific conditions on the basis of their ability to discriminate "cancer" from "non cancer" samples. This also shows that the test is robust to measurement noise and population diversity, which is a useful feature for the final product.

In certain embodiments of the invention, an individual is assayed for a certain number of markers to obtain methylation values for each marker of the certain markers. Then, based on those figures, one can with a high accuracy distinguish between "cancer" or "non cancer" case.

V. Kits of the Invention

Any of the compositions described herein may be comprised in a kit. In a non-limiting example, one or more reagents to determine methylation status of one or more genes may be comprised in a kit in suitable container means. The reagents may include primers, buffers, dinucleotides, labels, dyes, sequencing reagents, and/or microchips comprising one or more nucleic acids associated with the invention, one or more PCR reagents, and so forth.

The kit may include primers that target one or more regulatory areas of the genes described herein. This kit may be used in combination with any commercially available kit used for methylation quantification, such as QPCR SYBR® green Kit, QPCRTaqman KIT, QPCR HRM kit, QPCR FRET Kit, emulsion PCR KIT, high throughput library preparation kit, sequencing kit, hybridization kit for microarray or any software or script identifying the methylation of the genes cited below, for example.

The kits may comprise a suitably aliquoted composition of the present invention, where appropriate. The components of the kits may be packaged either in aqueous media or in lyophilized form. However, the components of the kit may be provided as dried powder(s). When reagents and/or components are provided as a dry powder, the powder can be reconstituted by the addition of a suitable solvent. It is envisioned that the solvent may also be provided in another container means.

The container means of the kits will generally include at least one vial, test tube, flask, bottle, syringe or other container means, into which a component may be placed, and in some embodiments, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the targeting peptide and/or active agent and any other reagent containers in close confinement for commercial sale. Such containers may include injection or blow molded plastic containers into which the desired vials are retained. The container means may itself be a syringe, pipette, and/or other such like apparatus, from which the formulation may be applied to the sample collected from the body.

In some embodiments, there are devices suitable for extraction of a sample from an individual, including by non-invasive means, for example. Such devices include swab (including rectal swab), phlebotomy material(s), scalpel, syringe, rod, and so forth.

The kit could also comprise any script or software using the analysis of the methylation of the target genes described herein.

EXAMPLES

The following examples are included to demonstrate some embodiments of the invention. It should be appreciated by those of skill in the art that the techniques disclosed in the examples which follow represent techniques discovered by the inventor to function well in the practice of the invention, and thus can be considered to constitute some modes for its practice. However, those of skill in the art should, in light of the present disclosure, appreciate that many changes can be made in the specific embodiments which are disclosed and still obtain a like or similar result without departing from the spirit and scope of the invention.

Example 1

Composite Biomarker for Non-Invasive Screening, Diagnosis and Prognosis of Colorectal Cancer In the present example, one or more biomarkers are identified for screening, diagnosis, and/or prognosis of colorectal cancer (CRC). The inventors identified a set of methylation-based biomarkers to enable non-invasive screening, diagnosis and/or prognosis of CRC. They used inferred correlation between expression profiles in tissue and methylation in serum using as an example Vimentin, a gene largely studied and the only commercially available diagnostic test based on DNA methylation (Colosure, Labcorp). Then, they apply this correlation to assess in silico the sensitivity and specificity of gene markers identified as being methylated in CRC. This method allowed identification of a set of genes with a strong diagnostic power when used in combination better than a Vimentin diagnostic kit.

Several methylated genes described in CRC patients were reported in tissue, but large cohort results on all of these genes are lacking, and few are investigated for methylation in serum. The inventors collected 95 genes considered relevant from more than 2200 publications. Using computational methods, they predicted the sensitivity and the specificity of these 95 genes in serum from their expression profile in tissue of CRC patients in adenoma stage versus normal subjects as assessed by an Affymetrix (Santa Clara, Calif.) microarray series available in Gene Expression Omnibus (GEO) (National Center for Biotechnology Information). From this set of 95 genes, the below 29 genes are statistically hypermethylated in Adenoma versus Normal with p value $<10^{-4}$, and they keep their ability to discriminate even at high methylation value thresholds: P15.INK4b (NCBI gene ID:1030), SST.SOMATOSTATIN (Gene ID: 6750), NPY (Gene ID: 4852), JAM2 (Gene ID: 58494), CNRIP1 (Gene ID: 25927), GAS7 (Gene ID: 8522), PIK3CG (Gene ID: 5294), MAL (Gene ID: 4118), LAMA1 (Gene ID: 284217), SLIT2 (Gene ID: 9353), RERG (Gene ID: 85004), IRF4 (Gene ID: 3662), ADHFE1 (Gene ID: 137872), COL1A2 (Gene ID: 1278), EPHA7 (Gene ID: 2045), RUNX3 (Gene ID: 864), MDR1(Gene ID: 5243), CHFR (Gene ID: 55743), N33.TUMOR_SUPPRESSOR_CANDIDATE_3 (Gene ID: 7991), RASSF2 (Gene ID: 9770), DAB21P (Gene ID: 153090), HPP1 (Gene ID: 23671), SFRP1(Gene ID: 6422), CXX1 (Gene ID: 8933), ESTROGEN_RECEPTOR_1 (Gene ID: 2099), FAS (Gene ID: 355), DSC3 (Gene ID: 1825), MUC2 (Gene ID: 4583), and RETINOIC_RECEPTOR_ACID_BETA_2 genes (Gene ID: 5915). At least several combinations of these 29 genes improve the sensitivity and specificity in detection of the adenoma stage (early stage) of CRC from healthy individuals. FIG. 1 presents the correlation of 32 patients and the methylation status (being at least above the highest methylation value in normal individuals). This demonstrates that the combination of these genes can enable one to discriminate patients with adenomas with 100% of specificity and 100% of sensitivity, which is better than the Vimentin gene alone (FIG. 1).

In certain embodiments, the inventors selected the 29 genes on the basis of two exemplary parameters: 1) the corrected statistical p-value in adenoma group versus normal group is $<10^{4}$; and 2) the gene is reported in published literature as being hypermethylated. In many cases, the gene is reported as hypermethylated in a single-gene study. Note that there is no single study that reports hypermethylation of the genes described herein. The inventors considered that at this exemplary p-value threshold, which is still stringent, one could capture genes that give high discrimination even in presence of noise (up to 33% of the difference between full methylation and highest methylation value in set of normal, for example).

One exemplary set of biomarkers that may be considered a base set, in some embodiments, comprises, consists essentially of, or consists of regulatory regions of the following 29 genes, namely: P15.INK4b (NCBI gene ID:1030), SST.SOMATOSTATIN (Gene ID: 6750), NPY (Gene ID: 4852), JAM2 (Gene ID: 58494), CNRIP1 (Gene ID: 25927), GAS7 (Gene ID: 8522), PIK3CG (Gene ID: 5294), MAL (Gene ID: 4118), LAMA1(Gene ID: 284217), SLIT2 (Gene ID: 9353), RERG (Gene ID: 85004), IRF4 (Gene ID: 3662), ADHFE1 (Gene ID: 137872), COL1A2 (Gene ID: 1278), EPHA7 (Gene ID: 2045), RUNX3 (Gene ID: 864), MDR1 (Gene ID: 5243), CHFR (Gene ID: 55743), N33.TUMOR_SUPPRESSOR_CANDIDATE_3 (Gene ID: 7991), RASSF2 (Gene ID: 9770), DAB21P (Gene ID: 153090), HPP1 (Gene ID: 23671), SFRP1(Gene ID: 6422), CXX1 (Gene ID: 8933), ESTROGEN_RECEPTOR_1 (Gene ID: 2099), FAS (Gene ID: 355), DSC3 (Gene ID: 1825), MUC2 (Gene ID: 4583), and RETINOIC_RECEPTOR_ACID_BETA_2 genes (Gene ID: 5915). In particular embodiments, the set to be assayed is less than all 29 of the listed genes, including 28, 27, 26, 25, 24, 23, 22, 21, 20, 19, 18, 17, 16, 15, 14, 13, 12, 11, 10, 9, 8, 7, 6, 5, 4, 3, 2, or 1 of the genes.

In specific embodiments, there are sub-combinations of these 29 genes that are useful in methods of the invention. In particular aspects, such embodiments were selected based on the following: 1) combination of five genes in base set, such that each patient has at least two positive calls (In embodiments of the invention, "positive call of a marker in a body fluid of a patient" is the fact that the methylation value of that marker measured in that body fluid (serum, urine, stool, etc.) of the patient is above a marker- and body fluid-specific threshold), and 2) to each combination the inventors added P15.INK4b, because all tested adenoma patients were hypermethylated for this marker. For example, Set1 was selected by using the top ranking 11 genes excluding Vimentin.

The set of the regulatory regions of the following genes is referred to as Set1: P15.INK4b, SST, NPY, JAM2, CNRIP1, GAS7, PIK3CG, MAL, LAMA1 and SLIT2.

The set of the regulatory regions of the following genes is referred to as Set2: P15.INK4b, SST.SOMATOSTATIN, JAM2, GAS7, CNRIP1 and PIK3CG.

The set of the regulatory regions of the following genes is referred to as Set3: P15.INK4b, SST.SOMATOSTATIN, GAS7, NPY, CNRIP1 and PIK3CG.

The set of the regulatory regions of the following genes is referred to as Set4: P15.INK4b, SST.SOMATOSTATIN, GAS7, CNRIP1, MAL and PIK3CG.

The set of the regulatory regions of the following genes is referred to as Set5: P15.INK4b, SST.SOMATOSTATIN, GAS7, CNRIP1, PIK3CG and LAMA1.

The set of the regulatory regions of the following genes is referred to as Set6: P15.INK4b, SST.SOMATOSTATIN. GAS7, CNRIP1, PIK3CG and RERG.

The set of the regulatory regions of the following genes is referred to as Set7: P15.INK4b, SST.SOMATOSTATIN, GAS7, CNRIP1, PIK3CG and SLIT2.

In embodiments of the invention, screening, diagnosis and/or prognosis of CRC can be performed by at least two markers using suitably chosen combinations of the methylation patterns from or with any of the markers from the Base set. In some embodiments, screening, diagnosis and prognosis of CRC can be performed by at least two positive calls using suitably chosen combinations of the markers containing at least two markers from or with the Base set. In certain embodiments, screening, diagnosis and prognosis of CRC can be performed by at least two positive calls using a combination of methylation patterns of markers from or with Set1, Set2, Set3, Set4, Set5, Set6, or Set7, for example.

In embodiments of the invention, the methylation patterns of different combinations of at least two genes from Set 1 to Set 9, for example, enable highly accurate screening, diagnosis and prognosis of CRC with any sufficiently high methylation values. The patterns of different combination of at least two genes described herein enable sufficiently accurate screening, diagnosis and/or prognosis of CRC with thresholds obtained by adding to each biomarker's threshold in a given body fluid, respectively, 5%, 10%, 20%, 25% or 33% of the difference between full methylation state and the maximum methylation value observed in the group of normal.

In embodiments of the invention, using combinations of the methylation patterns of genes encoding transcription factors, genes encoding TF binding proteins (TFBP) and/or genes encoding transcription cofactors that regulate expression of any marker in the Base set (and/or of markers in other subcombinations herein) significantly improves accuracy of screening, diagnosis and/or prognosis of CRC.

In embodiments of the invention, one can use combinations of the methylation patterns of genes belonging to the following signaling pathways: P53 signaling pathway, Wnt signaling pathway, Cytokine signaling pathways (EGF/FGF/IGF/PDGF/VEGF/Insulin signaling pathways), Angiogenesis signaling pathway, and Apoptosis signalling significantly improve accuracy of screening, diagnosis and/or prognosis of CRC. These pathways are significantly enriched in genes from Base set in certain embodiments. Each of these pathways contains four genes from Base set.

In some embodiments of the invention, using combinations of the methylation patterns of at least 2 genes encoding transcription factors, transcription cofactors, or transcription factor binding proteins regulate any of the genes described herein allow for accurate screening, diagnosis and/or prognosis of CRC.

The sample from an individual can be assayed in tissue, blood, serum, plasma, spittle, stool, urine, or any other body fluid, for example. In some aspects, the invention uses any appropriate method to extract and concentrate nucleic acids from body fluids or any method to assess methylation directly from the body fluids. Methods to target the specific nucleic acids that correspond to one or more of the genes in the base set are well known in the art. Furthermore, methods to quantify the level of methylation of the target sequences are also well known in the art.

REFERENCES

All patents and publications mentioned in the specification are indicative of the level of those skilled in the art to which the invention pertains. All patents and publications are herein incorporated by reference in their entirety to the same extent as if each individual publication was specifically and individually indicated to be incorporated by reference.

PATENTS

U.S. Pat. No. 4,458,066

PUBLICATIONS

Beaucage, S. L.; Caruthers M. H. (1981). "Deoxynucleoside phosphoramidites—A new class of key intermediates for deoxypolynucleotide synthesis". Tetrahedron Letters 22: 1859-1862.

Conner B J, et al., Detection of sickle cell beta S-globin allele by hybridization with synthetic oligonucleotides. Proc Natl Acad Sci USA. 1983 January; 80(1):278-82.

Dallol, A., et al., SLIT2 Axon Guidance Molecule is Frequently Inactivatedi n Colorectal Cancer and Suppresses Growth of Colorectal Carcinoma Cells, Cancer Res. (2003), 63:1054-1058.

Eads, C. A. et al., CpG island hypermethylation in human colorectal tumors is not associated with DNA methyltransferase overexpression. Cancer Res. 59:2302-2306, 1999.

Frommer, M. et al. A genomic sequencing protocol that yields a positive display of 5-methylcytosine residues in individual DNA strands. Proc. Natl. Acad. Sci. USA 89:1827-1831, 1992.

Goel, A., et al., Epigenetic Inactivation of RUNX3 in Microsatellite Unstable Sporadic Colon Cancers, Int. J. Cancer (2004), 112:754-759.

Gonzalgo, M. L. and Jones, P. A., Rapid quantitation of methylation differences at specific sites using methylation-sensitive single nucleotide primer extension (Ms-SNuPE). Nucleic Acids Res. 25:2529-2531, 1997.

Green et al., "Nuclease-resistant nucleic acid ligands to vascular permeability factorvascular endothelial growth factor", Chem. Biol., 2:683-695 (1995).

Herman, J. G., et al., Methylation-specific PCR: a Novel PCR Assay for Methylation Status of CpG Islands, Proc. Natl. Acad Sci, 93:9821-6.

Ishiguro, A., et al., Influence of Methylated p15 and p16 Genes on Clinicopathological Features in Colorectal Cancer (2006), 21(8):1334-9.

Kim, Y.-H., et al., Epigenomic Analysis of Aberrantly Methylated Genes in Colorectal Cancer Identifies Genes Commonly Affected by Epigenetic Alterations, Ann Surg Oncol (2011), 18:2338-2347.

Klobmann et al., Nature Biotechnol., 14:1112-1115 (1996).

Kuhn B, Abdel-Monem M, Hoffmann-Berling H. DNA Helicases. Cold Spring Harb Symp Quant Biol. 1979; 43 Pt 1:63-7.

Landegren, U. et al., A ligase-mediated gene detection technique. Science, 241:1077, 1988.

Landegren, U. et al., "DNA Diagnostics—Molecular Techniques and Automation," Science 242:229-237 (1988).

Maniatis, T., et al. Molecular Cloning: A Laboratory Manual, Cold Spring Harbor, N.Y., pp 280, 281, 1982.

Nolte et al., "Mirror-design of L-oligonucleotide ligands binding to L-arginine," Nature Biotechnology 14:1116-1119 (1996).

Oster, B., et al., Identification and Validation of Highly Frequent CpG Island Hypermethylation in Colorectal Adenomas and Carcinomas, Int. J. Cancer (2011), in press.

Pagratis et al., "Potent 2'-amino-, and 2'-fluoro-2'-deoxyribonucleotide RNA inhibitors of keratinocyte growth factor," Nature Biotechnology 15:68-73 (1997).

Piekern, Ann. Rev. Biochem., 64:837-863 (1995).

Radding, C. Homologous pairing and strand exchange in genetic recombination. Ann. Rev. Genetics, 16:405-437, 1982.

Reed et al., Cancer Res. 50:6565-6570 (1990).

Remontet et al. Evolution de l' incidence de la mortalité par cancer 2003; (www.insv.sante.fr)—Globocan 2008, Cancer Incidence and Mortality Worldwide, WHO Sadri, R. and Hornsby, P. J. Rapid analysis of DNA methylation using new restriction enzyme sites created by bisulfite modification. Nucl. Acids Res. 24:5058-5059, 1996.

Saiki, R. K. et al., A Novel Method for the Detection of Polymorphic Restriction Sites by Cleavage of Oligonucleotide Probes: Application to Sickle-Cell Anemia, BioTechnology, 3, 1008-1012 (1985).

Tam et al., Nucl. Acids Res., 22:977-986 (1994).

Toyota, M. et al., Identification of differentially methylated sequences in colorectal cancer by methylated CpG island amplification. Cancer Res. 59:2307-12, 1999.

Xiong, Z. and Laird, P. W., COBRA: a sensitive and quantitative DNA methylation assay. Nucleic Acids Res. 25:2532-2534, 1997.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method comprising:

(a) measuring, in a sample obtained from an individual, a methylation level in a CpG promoter island of each gene in a set of genes, wherein the set of genes consists of P15.INK4b, somatostatin, GAS7, CNRIP1, PIK3CG, NPY, JAM2, MAL, LAMA1, SLIT2, and RERG, and (b) administering to the individual a therapy in an amount effective to treat colorectal cancer, wherein the therapy is selected from the group consisting of surgery, chemotherapy, radiation, gene therapy, or a combination thereof.

2. The method of claim 1, wherein the sample is selected from the group consisting of tissue, blood, spittle, serum, plasma, urine, sputum, biopsy and stool.

3. The method of claim 1, wherein the individual is 50 years or older in age.

4. The method of claim 1, wherein the individual has one or more symptoms of colorectal cancer.

5. The method of claim 1, wherein the individual has a prior history of having cancer.

6. The method of claim 4, wherein the one or more symptoms is selected from the group consisting of a change in bowel habits, constipation that lasts more than a couple of weeks, diarrhea that lasts more than a couple of weeks, a feeling that the bowel does not empty completely, blood in the stool, narrow or thinner than normal stool, abdominal discomfort, gas pains, bloating, fullness, cramps, weight loss, fatigue, anemia, and a combination thereof.

7. The method of claim 1, wherein the individual has a personal or family history of colorectal cancer, has or has had colon polyps, bowel inflammatory disease, or is or was positive for hemoccult test.

8. The method of claim 1, wherein the individual has a personal or family history of familial adenomatous polyposis, Lynch syndrome, Peutz-Jeghers syndrome or juvenile polyposis syndrome.

9. The method of claim 1, wherein the individual has colorectal cancer that originates in the colon of the individual.

10. The method of claim 1, wherein the individual has colorectal cancer that originates in the rectum of the individual.

11. The method of claim 1, wherein the individual has stage 0, 1, 2, 3, or 4 colorectal cancer.

12. The method of claim 1, wherein the methylation levels are determined by methylation specific polymerization chain reaction, methyl-BEAMing, COBRA, or methylated CpG island amplification.

* * * * *